United States Patent [19]

Krauss

[11] 4,131,019
[45] Dec. 26, 1978

[54] METHOD AND APPARATUS FOR MEASURING SPECIFIC GRAVITY OF LIQUIDS IN PROCESS STREAMS

[75] Inventor: Clifford J. Krauss, Trail, Canada

[73] Assignee: Cominco Ltd., Vancouver, Canada

[21] Appl. No.: 778,917

[22] Filed: Mar. 17, 1977

Related U.S. Application Data

[63] Continuation-in-part of Ser. No. 652,912, Jan. 28, 1976, abandoned.

[30] Foreign Application Priority Data

Apr. 10, 1975 [CA] Canada .................................. 224552

[51] Int. Cl.² .............................................. G01N 9/18
[52] U.S. Cl. ...................................................... 73/453
[58] Field of Search ......................... 73/445, 452, 453; 336/136, 105

[56] References Cited

U.S. PATENT DOCUMENTS

| | | | |
|---|---|---|---|
| 2,273,850 | 2/1942 | Ewald | 73/453 |
| 2,362,661 | 11/1944 | Peters | 73/453 |
| 2,703,494 | 3/1955 | Carney | 73/452 X |
| 3,235,790 | 2/1966 | Collins | 336/105 |
| 3,661,015 | 5/1972 | Paul | 73/445 |
| 3,952,761 | 4/1976 | Friedland | 73/452 |

FOREIGN PATENT DOCUMENTS

| | | | |
|---|---|---|---|
| 283593 | 4/1915 | Fed. Rep. of Germany | 73/445 |
| 431424 | 11/1971 | U.S.S.R. | 73/453 |

*Primary Examiner*—S. Clement Swisher
*Attorney, Agent, or Firm*—Arne I. Fors

[57] ABSTRACT

A method and apparatus for measuring the specific gravity of liquids in process streams by intermittently sampling the process stream and measuring the specific gravity of the sampled liquid under static conditions in a constant level overflow device by the use of a variable immersion hydrometer operatively connected to a linear voltage displacement transducer, i.e. differential transformer, whereby vertical displacement of the hydrometer results in an output voltage signal indicative of the specific gravity of the sampled liquid. Means can be provided for compensating the specific gravity for ambient and liquid temperature and for controlling and recording the specific gravity of the liquid.

2 Claims, 2 Drawing Figures

METHOD AND APPARATUS FOR MEASURING SPECIFIC GRAVITY OF LIQUIDS IN PROCESS STREAMS

This application is a continuation-in-part of application Ser. No. 652,912 filed Jan. 28, 1976 now abandoned.

BACKGROUND OF THE INVENTION

This invention relates to a method and apparatus for determining the specific gravity of liquids and more particularly relates to a method and apparatus for accurately determining the specific gravity of liquid and solution process streams.

The specific gravity of liquids can be measured by using any one of a large number of methods and apparatus. One of the simplest of these is the use of a variable immersion hydrometer placed directly in the liquid whose specific gravity is to be measured. The degree of immersion of the hydrometer is an indication of the specific gravity of the liquid. The accuracy of the measurement and of the specific gravity are a function of such liquid properties as surface tension, turbulence, composition, purity and temperature.

The variable immersion hydrometer may be positioned in a rotameter housing and may be equipped with an electronic circuit based on measurement of impedance or capacitance. Automatic temperature compensation may also be provided.

The prior art discloses many methods for measuring the specific gravity of liquids based on the variable immersion hydrometer equipped with electronic transmission of a signal proportional to the specific gravity of the liquid. However, the methods and apparatus are usually complex and often have a limited accuracy. For example, in U.S. Pat. No. 3,392,589 which issued on July 16, 1968 to L. E. Kuntz et al., there is disclosed an apparatus for continuously determining the specific gravity of a product stream which comprises a constant overflow chamber, a hydrometer, an electrical capacitance variable by the hydrometer in relation to its immersion, and means for translating the capacitance into a signal representative of the liquid density. The apparatus also includes means for sensing liquid temperature and generating a further signal which, in combination with the density representative signal, forms a third signal representative of the specific gravity of the liquid at a predetermined temperature. This method is complex as it necessitates the translation of the capacitance into another signal.

In many processes it is necessary to measure the specific gravity or strength of process liquids with great accuracy. The ability of the electrical, nuclear and other devices to measure specific gravity accurately depends greatly on the signal to noise ratio of the device. Where this ratio is high, a high degree of accuracy can be attained. However, most measuring devices have a low ratio and, in addition, have high drift characteristics which make frequent calibration necessary.

Another prerequisite for the accurate measurement of liquid specific gravity is the need for preventing undesirable movements of the hydrometer. Thus, a high degree of accuracy is difficult to obtain in measurement in a continuous fashion in a flowing process stream, as this entails measurement in a moving body of liquid which is usually subject to fluctuations in the rate of flow of the liquid. Measurement in a batchwise fashion, for example, by withdrawing a sample and measuring the specific gravity in the sample, is not only time consuming but makes control difficult, although the desired degree of accuracy might be obtained.

Still another prerequisite is the need for linearity of the measuring system. Many measuring systems, such as for example Wheatstone bridges, do not usually provide the required degree of linearity and require compensating means.

STATEMENT OF INVENTION

I have now discovered that the disadvantages of the methods and devices according to the prior art can be alleviated by using a variable immersion-type hydrometer in combination with a linear voltage displacement transducer (LVDT) which intermittently senses the position of the hydrometer and provides a voltage signal directly representative of the specific gravity of a process liquid. Intermittent, i.e. semicontinuous, measurement of specific gravity of the liquid of the process stream, in order to obtain more representative measurement of liquid specific gravity, provides a stationary body of liquid, wherein undesirable movement of the hydrometer is obviated and whereby the desired high degree of accuracy necessary to closely control the specific gravity of liquids in process streams is obtained.

It is therefore a principal object of the present invention to accurately measure the specific gravity of a liquid in a process stream.

It is another object to intermittently determine the specific gravity of a liquid in a process stream and to compensate the same for the effect of stream temperature.

It is still another object of the invention to provide a method and an apparatus to accurately measure the specific gravity of a liquid in a process stream, to compensate the same for the effect of ambient temperature and for the effect of temperature of the liquid in the process stream, and to control the specific gravity of the liquid.

It is yet another object of the invention to specifically measure and control the specific gravity of process streams of sulphuric acid solutions.

These and other objects of the invention and the manner in which they can be attained will become apparent from the following detailed description of the method and apparatus of the invention.

According to the method of the invention, there is provided a method for intermittently measuring the specific gravity of a liquid in a process stream which comprises the steps of immersing a variable immersion hydrometer in said liquid contained in a constant level overflow device, said hydrometer being operatively connected to a core forming part of a linear voltage displacement transducer, i.e. differential transformer, applying a constant voltage to said linear voltage displacement transducer, and measuring the output voltage in response to the vertical position of the hydrometer and core, said output voltage representing the specific gravity of the process liquid in the overflow device while the said liquid is stationary.

The apparatus to measure the specific gravity of a liquid in a process stream comprises, in combination, a process liquid line, a constant level overflow device, means interconnecting the process liquid line and overflow device for intermittently supplying a volume of process liquid to fill said overflow device and for displacing process liquid from said overflow device, a variable immersion hydrometer positioned in said constant level overflow device, a linear voltage displacement transducer having a core loosely embraced therein, said core being operatively connected to said hydrometer, whereby said hydrometer and core are vertically displaced dependent on the specific gravity of the process liquid, and a source of constant voltage electrically connected to said linear voltage displacement transducer whereby an output voltage signal is emitted by said linear voltage displacement transducer proportional to the position of the core therein, said output voltage signal varying directly with the specific gravity of the liquid.

BRIEF DESCRIPTION OF THE DRAWING

The invention will now be described with reference to the accompanying drawing, in which.

DESCRIPTION OF THE PREFERRED EMBODIMENT

Figure 1:
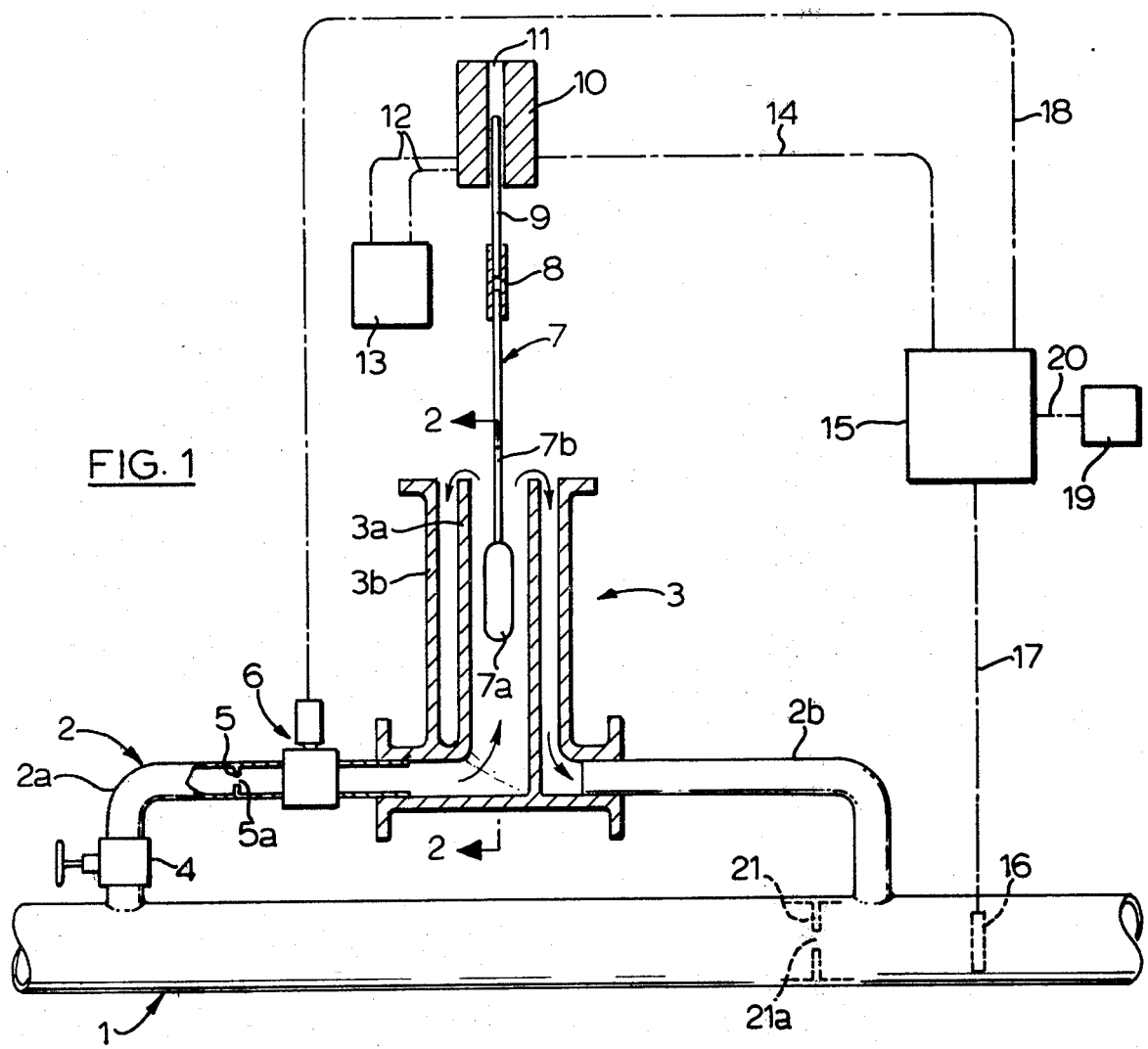
FIG. 1 is an elevation, partly cut away, which schematically illustrates the method and apparatus of the invention.

With reference first to FIG. 1, the process liquid of which the specific gravity is to be measured flows through a process line 1. A portion of the liquid is diverted from the process line through a sample line generally designated by numeral 2. The diverted portion flows through a first portion 2a of sample line 2, through a constant level overflow chamber generally designated by numeral 3 and returns to process line 1 through a second portion 2b of sample line 2. The diverted liquid portion is returned to process line downstream from the point of diversion. To control the flow of liquid through the process line, an orifice plate 21 with orifice 21a may be positioned in the portion of the process line between the point of diversion and the point of return of the diverted liquid.

Portion 2a of sample line 2 is provided with a shut-off valve 4, an orifice plate 5 with an orifice 5a and an on-off flow control valve 6. Valve 4 is open during normal operation but may be closed to isolate sample line 2 when necessary. The size of orifice 5a is chosen such that the pressure drop over the orifice is sufficient to allow overflow chamber 3 to operate under atmospheric pressure. On-off control valve 6 is alternately opened and closed for predetermined periods of time to provide a first period of static conditions in the chamber which allows accurate measurement of specific gravity and to provide a subsequent period of time during which to flush out the liquid present in the chamber and to allow a fresh amount of liquid to enter the chamber.

Figure 2:
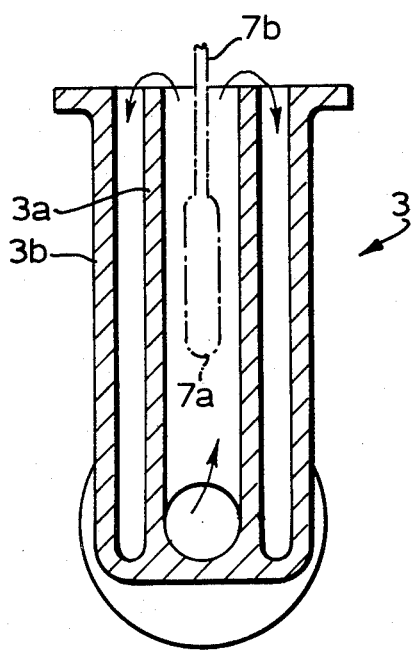
FIG. 2 is a section, taken along line 2—2 of FIG. 1, of the overflow chamber of the invention.

With reference now also to FIG. 2, overflow chamber 3 may be made in one piece and is fitted between sections 2a and 2b in sample line 2. Constant overflow chamber 3 consists of two concentric tubular members 3a and 3b. The inner tubular member 3a is connected to portion 2a of the sample line 2 and outer tubular member 3b is connected to portion 2b of sample line 2, members 3a and 3b being connected in such a way that liquid from line 2a flows into and upward through inner member 3a over its top into outer member 3b, downward through member 3b and out into line 2b. The cross-sectional area of the annulus between members 3a and 3b is usually about the same as the cross-sectional area of inner member 3a but may be larger to ensure liquid does not overflow from the chamber. The cross-sectional area of inner member 3a should be large enough so that a hydrometer placed in the liquid in inner member 3a does not interfere with the flow of liquid through member 3a. The top of tubular member 3b may be equal with or slightly higher or lower than the top of tubular member 3a. Preferably the top of tubular member 3b is slightly lower than that of member 3a.

A variable immersion hydrometer generally indicated by numeral 7 is positioned in inner tubular member 3a of overflow chamber 3. Hydrometer 7 may be of the standard type made of a material substantially inert to the liquid to be measured and is chosen such that its measuring range covers the desired range of specific gravities of the liquid flowing through process line 1. The hydrometer consists of a submergible weighted bulbous portion 7a and a stem 7b extending upwardly therefrom. The bulbous portion 7a is submerged in the liquid in inner member 3a of chamber 3, while the stem is only partly immersed; the degree of immersion being dependent on the specific gravity of the liquid.

The top end of the exposed portion of stem 7b is connected by a coupling 8 to a metallic core member 9, which comprises a part of a linear voltage displacement transducer (LVDT) 10. Coupling 8 is preferably a sleeve made of a flexible material such as, for example, rubber or plastic tubing.

Core 9 inserts loosely and freely movable into the core channel 11 of LVDT 10, so that the channel 11 embraces, i.e. envelops, at least a portion of core 9. An LVDT is an extremely sensitive device which, in the scope of the method and apparatus of the present invention, will be understood to comprise a DC-input, DC-output differential transformer with built-in carrier oscillator and phase sensitive demodulator providing DC output proportional to linear displacement. When a constant DC voltage is applied, the oscillator converts the DC input power to AC which is used to excite the primary winding. The axial core position determines the amount of voltage induced in the secondary windings. Each of the two secondary circuits contains a secondary winding, a full-wave bridge, and an RC filter. These secondary circuits are connected in series opposition so that the resultant output is a DC voltage proportional to the core displacement. The output voltage signal is constant with each position of the core. The output voltage signal also varies directly proportional to the position of the core in the channel, i.e. changes with a constant number of millivolts for each unit of travel of the core (mv/mm). An LVDT has a very high signal to noise ratio, as well as very low zero-drift characteristics. These properties of an LVDT provide a high degree of accuracy and necessitate very infrequent calibrations.

In addition, small displacement of the core results in a large output signal change providing a high sensitivity to small changes in liquid specific gravity. For example, a 1 millimeter linear displacement of the core may result in the change of an output signal from the LVDT in the range of from 100 to 2000 millivolts, depending on the LVDT model being used. Consequently, a small vertical displacement of the hydrometer due to a change in liquid specific gravity can be detected with very great accuracy. This sensitivity enables the measurement of liquid specific gravity with an accuracy down to the fourth decimal. An LVDT also provides built-in correction for variations in ambient temperature.

A constant excitation voltage supply source 13, such as, for example, a constant voltage power supply or an ordinary dry or wet-cell battery, is connected to LVDT 10 with lead wires 12.

LVDT 10 may be connected to an indicator (not shown) which indicates the output signal in millivolts which is proportional to the specific gravity of the liquid. If so desired, the indicator may be calibrated to indicate specific gravity directly. Alternatively, LVDT 10 may be connected by lead 14 to conventional computer 15. The output signal from the LVDT is computed in computer 15 into liquid specific gravity corrected for changes in liquid temperature. Changes in liquid temperature are sensed by temperature sensor 16 placed in the liquid in process line 1 and are transmitted to the computer by lead 17. Alternatively, the temperature sensor may be positioned in chamber 3. The computer also controls the opening and closing of on-off control valve 6 and the lengths of the periods during which valve 6 is open and closed. On-off valve 6 is connected to computer 15 by lead 18. If so desired, on-off valve 6 may be controlled by a separate timing device (not shown).

The computed and temperature corrected liquid specific gravity data are transmitted to means 19 by lead 20 for either indicating, recording, or controlling, or any combination of these three functions, of the specific gravity of the liquid. In case of means 19 having the controlling function, a feed-back signal is used to control the specific gravity of the process stream. Measurement of liquid specific gravity with an accuracy to the fourth decimal enables control of the specific gravity with an accuracy down to the third decimal.

In the method of the invention, shut-off valve 4 is open during operation. On-off valve 6 is alternately opened and closed on signals of computer 15 to provide alternately open and closed positions of the valve for suitable periods of equal or unequal duration which may, for example, range from 15 to 120 seconds. During the open period of valve 6, liquid from line 1 flows through sample line 2 and the overflow chamber 3, and displaces the liquid present in the chamber from the previous period. Valve 6 subsequently closes, the liquid in chamber 3 stabilizes and the hydrometer 7 with the attached core member 9 in channel 11 of LVDT 10 attains a stationary position. The position of the core in the LVDT with the constant voltage input from voltage source 13 creates an output signal in millivolts, which is directly representative of the specific gravity of the liquid and which is transmitted to computer 15. In the computer the LVDT signal is corrected for deviation of the temperature from the standard by a signal from sensor 16 transmitted through lead 17 which is translated into temperature corrected liquid specific gravity which, in turn, is indicated and/or recorded via lead 20 by means 19, or which is used by means 19 to control the liquid specific gravity of the process stream by means of a feedback signal.

The method and apparatus of the invention can be successfully applied in the measuring of densities of process liquids.

The invention will now be illustrated by means of the following examples.

EXAMPLE 1

The method and apparatus are used for measuring the specific gravity and for controlling the strength of sulphuric acid in process streams of a sulphuric acid production unit. The apparatus is according to the above description.

A ½ inch (12.7 mm) sample line is connected at two points into a 4 inch (102 mm) process line and is provided with a shut-off valve, an on-off control valve and a constant overflow chamber having an inner tubular member with a diameter of 2 inches (51 mm) and an outer tubular member with a diameter of 4.25 inches (108 mm). The flow of acid through the process line is controlled by a 1¾ inch (45 mm) orifice placed in the process line between the connection points of the sample line. A ⅜ inch (9.5 mm) orifice in the sample line controls the acid flow through the sample line and the constant overflow chamber at 75 ml/sec. The on-off control valve operates on signals from a timing device which cause the valve to alternately open and close for periods of 30 seconds. A glass hydrometer with a calibrated scale for specific gravity S.G. 20° C./4 of from 1.800 to 1.830 is used in the constant overflow chamber.

The LVDT used is a Hewlett Packard Model No. 7 DCDT-100 which is supplied with a constant excitation voltage of 6 volts and which can emit a signal over a range of 0 to 4800 mv for a linear displacement of its core, which is attached to the hydrometer, of from 0 to 50 mm. The output voltage signal from the LVDT is transmitted to an IBM (Trade Mark) computer model No. 1800 and the signal is corrected by the computer for temperature deviations in the acid in the process line as measured with a thermistor placed in the acid flowing through the overflow chamber. The temperature of the acid varies from about 20 to about 40° C. The temperature of the acid, the specific gravity of the acid and the strength of the acid can be indicated or recorded. A feedback signal based on the temperature corrected specific gravity of the acid is used to control the strength of the acid in the process line by addition of water or concentrated acid, as required. In this manner the strength of the sulphuric acid is controlled within ± 0.2%, e.g. 93.0% ± 0.2%.

EXAMPLE 2

The same method and apparatus as used in Example 1 are used to measure and indicate the specific gravity of return acid in the process for the electrowinning of zinc, the only difference being the hydrometer which has a range for specific gravity 20° C./4 of from 1.220 to 1.260.

Changes in the specific gravity of return acid indicate either a change in acid concentration or a change in the addition of water, both of which have undesirable effects on the efficiency of the electrowinning process.

The specific gravity of the return acid is controlled with an accuracy of 0.004, e.g. 1.240 ± 0.004.

It will be understood that the term "specific gravity" used in the foregoing description and appendant claims will include "relative specific gravity", i.e. density, of liquids to be measured.

What I claim as new and desire to protect by Letters Patent of the United States is:

1. An apparatus for measuring the specific gravity of a liquid from a process stream which comprises, in combination, a process liquid line, a constant level overflow device, means interconnecting the process liquid line and overflow device for intermittently supplying a volume of process liquid to fill said overflow device and for displacing process liquid from said overflow device, a variable immersion hydrometer positioned in said constant level overflow device, a linear voltage displacement transducer consisting of a differential transformer with built-in carrier oscillator and phase-sensitive demodulator having a core loosely embraced therein, said immersion hydrometer consisting of a submergible weighted bulbous portion and a stem extending upwardly therefrom, and flexible coupling means for connecting the core to the stem, whereby said hydrometer and core are vertically displaced dependent on the specific gravity of the process liquid, and a source of constant voltage electrically connected to said linear voltage displacement transducer whereby an output voltage signal is emitted by said linear voltage displacement transducer proportional to the position of the core therein, said output voltage signal varying directly with the specific gravity of the liquid measured.

2. An apparatus as claimed in claim 1 in which said flexible coupling means comprises a sleeve of rubber or plastic tubing.

* * * * *